(12) United States Patent
Karasawa

(10) Patent No.: US 7,173,238 B2
(45) Date of Patent: Feb. 6, 2007

(54) QC PHANTOM

(75) Inventor: Hiroyuki Karasawa, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 133 days.

(21) Appl. No.: 10/859,137

(22) Filed: Jun. 3, 2004

(65) Prior Publication Data

US 2004/0245447 A1 Dec. 9, 2004

(30) Foreign Application Priority Data

Jun. 3, 2003 (JP) ............................. 2003-158447

(51) Int. Cl.
*A61B 6/00* (2006.01)
(52) U.S. Cl. .................................. 250/252.1
(58) Field of Classification Search ................. 378/207; 250/252.1
See application file for complete search history.

(56) References Cited

U.S. PATENT DOCUMENTS 4,055,771 A * 10/1977 Goodenough et al. ........ 378/18
5,095,499 A 3/1992 Wentz
5,544,157 A 8/1996 Wenstrup et al.
5,799,059 A 8/1998 Stembridge et al.
6,694,047 B1 2/2004 Farrokhnia et al.
2003/0086626 A1 5/2003 Yamada

FOREIGN PATENT DOCUMENTS

| EP | 1 136 843 A2 | 9/2001 |
| FR | 2 796 480 A | 1/2001 |
| JP | 1-148241 A | 6/1989 |
| JP | 2001-299736 A | 10/2001 |

* cited by examiner

*Primary Examiner*—Constantine Hannaher
(74) *Attorney, Agent, or Firm*—Sughrue Mion, PLLC

(57) ABSTRACT

The phantom for quality control used to perform verification of performance and invariance of a radiation imaging system includes substrates and image quality evaluation patterns fixed to the substrates. The patterns is photographed with the system and images obtained by photographing is evaluated based on image quality evaluation items. A coefficient of linear expansion $\alpha_p$ of each of corresponding patterns fixed to each of the substrates and a coefficient of linear expansion $\alpha_s$ of each of the substrates to which the corresponding patterns are fixed, are in a relation of $|\alpha_p - \alpha_s| \leq 5 \times 10^{-5}$.

19 Claims, 3 Drawing Sheets

QC PHANTOM

BACKGROUND OF THE INVENTION

1. Field of the Invention

The present invention relates to a phantom for quality control or QC phantom used to perform quality assurance of a radiation imaging system that uses radiation or in particular X-rays.

2. Description of the Related Art

Digital radiography (DR) or in particular a digital radiation imaging system (hereinafter referred to as the "computed radiography (CR) system") that uses a photostimulable phosphor has been more and more widely used as a method replacing conventionally used radiography based on an intensifying screen and a silver salt film.

In this CR system, radiation that has passed through or has been emitted from a subject is absorbed into a radiation image conversion panel containing a photostimulable phosphor, the absorbed energy is emitted as fluorescence through excitation of the panel using excitation light such as infrared rays, and this fluorescence is read as a digital image through conversion into an electric signal.

With such a CR system, it is possible to obtain a digital image having an abundant amount of information, so that it is possible to carry out sophisticated medical diagnosis, for instance. In addition, it is also possible to transmit/receive the digital image as digital data, so that this system is also effective in remote medical care or the like.

By the way, in order to assure use of an X-ray image with a high degree of reliability, it is required to measure and verify the performance of the CR system. If image quality of the CR system is low, high-reliability image analysis is impossible. This is because an image that is low in reliability and unusable is generated owing to lowering of image contrast quality, for instance.

In order to solve this problem, measurement of parameters of the CR system is performed using a QC phantom. This QC phantom includes various image quality evaluation patterns fixed on a substrate. Those image quality evaluation patterns have characteristics such as sizes, shapes, densities, and compositions, are formed using various materials, are designed so that one or more image quality evaluation items of the CR system can be measured, and are set so that an invariance evaluation of different performance parameters of the CR system can be performed.

That is, first, the QC phantom is irradiated between a radiation source and a radiation image conversion panel. Then, image reading is performed, thereby obtaining a digital image in which the image quality evaluation patterns are captured, and a reproduction image thereof. Following this, a quantitative or visual image evaluation is performed, thereby performing a performance evaluation/image evaluation.

As examples of such a QC phantom, there are known a QC phantom disclosed in JP 01-148241 A that protects a resolving power chart made of tungsten in a methacrylic resin and a QC phantom disclosed in JP 2001-299736 A that uses a photoetching metal that is considered to have less distortion due to heat.

When image quality evaluation patterns made of metallic materials are fixed in a resin like in the case of the QC phantom disclosed in JP 01-148241 A, however, cracking may occur to the image quality evaluation patterns owing to differences in coefficient of thermal expansion between the metals and the resin.

Also, when resin patterns are fixed on a metal, for instance, this results in a situation where even if the coefficient of thermal expansion of the metal itself is small, peeling tends to occur owing to differences in coefficient of thermal expansion between the metal and the resins.

It is of course possible to fix the image quality evaluation patterns using structural members such as screws in order to increase fixation strength. In this case, however, such structural members are also captured at the time of X-ray imaging and therefore this construction is not appropriate.

SUMMARY OF THE INVENTION

The present invention has been made in view of the circumstances described above, and an object of the present invention is to provide a QC phantom that is capable of preventing cracking and peeling of image quality evaluation patterns with reliability and obtaining an X-ray image where no construction members other than the image quality evaluation patterns are captured.

It should be noted here that the above object and other objects as well as novel features of the present invention will become apparent from the following description to be made with reference to the accompanying drawings.

In order to achieve the above object, the present invention provides a phantom for quality control used to perform verification of performance and invariance of a radiation imaging system, comprising:

substrates; and image quality evaluation patterns fixed to the substrates, the image quality evaluation patterns being photographed with the radiation imaging system and pattern images obtained by photographing the image quality evaluation patterns being evaluated based on image quality evaluation items, wherein a coefficient of linear expansion $\alpha_p$ of each of corresponding image quality evaluation patterns which are fixed to each of the substrates and a coefficient of linear expansion $\alpha_s$ of each of the substrates to which the corresponding image quality evaluation patterns are fixed, are in a relation of $$|\alpha_p - \alpha_s| \leq 5 \times 10^{-5}.$$

The coefficient of linear expansion $\alpha_p$ of each of the corresponding image quality evaluation patterns and the coefficient of linear expansion $\alpha_s$ of each of the substrates are preferably in a relation of $$|\alpha_p - \alpha_s| \leq 2.5 \times 10^{-5}.$$

The coefficient of linear expansion $\alpha_p$ of each of the corresponding image quality evaluation patterns and the coefficient of linear expansion $\alpha_s$ of each of the substrates are more preferably in a relation of $$|\alpha_p - \alpha_s| \leq 1.5 \times 10^{-5}.$$

The image quality evaluation patterns are preferably fixed to the substrates by welding or bonding an image quality evaluation pattern on a substrate, alternatively, by molding integrally the image quality evaluation pattern with the substrate or forming the image quality evaluation pattern and the substrate through cutting by an NC machine tool.

The applicant proposes a QC phantom which has patterns made of different materials including an edge pattern or the like for use in sharpness measurement being made of a metal and a Burger pattern or the like for use in relative contrast measurement being made of a resin, and which is capable of many kinds of image quality evaluations upon being once photographed.

The present invention is particularly effective in this case.

In the phantom for quality control according to the present invention, the image quality evaluation patterns comprises first image quality evaluation patterns each made of a material or materials having a high radiation absorption rate; and second image quality evaluation patterns each made of a material or materials having a low radiation absorption rate.

Preferably, the first image quality evaluation patterns are made of a metal or metals and the second image quality evaluation patterns are made of a resin or resins.

It is preferred that the phantom for quality control of the present invention further comprises a rectangular frame member having a hollow portion; the substrates includes a first rectangular substrate made of a metal and provided in the hollow portion of the rectangular frame member and a rectangular top plate made of a resin and placed in the hollow portion of the rectangular frame member to oppose the first rectangular substrate with a preset distance between the rectangular top plate and the first rectangular substrate, the rectangular top plate serving as a second substrate; and that, in a hollow space formed by the rectangular frame member, the first rectangular substrate and the rectangular top plate, the first image quality evaluation patterns are fixed to an upper surface of the first rectangular substrate and the second image quality evaluation patterns are fixed to a lower surface of the rectangular top plate.

Preferably, peripheral ends of the first rectangular substrate and the rectangular top plate are partially fixed to the rectangular frame member under a state where the peripheral ends are fitted into an inner peripheral portion of the rectangular frame member.

The first rectangular substrate and the rectangular top plate are preferably disposed on an inside in a thickness direction of the rectangular frame member.

It is preferred that the phantom for quality control of the present invention further comprises a supporting plate for supporting the first rectangular substrate, the supporting plate is made of a resin and placed in the hollow portion of the rectangular frame member to oppose the first rectangular substrate, and that the first rectangular substrate is mounted on the supporting plate.

It is preferred that the phantom for quality control of the present invention further comprises a box-shaped frame member having an opening portion; the substrates includes a first rectangular substrate made of a metal and provided in the opening portion of the box-shaped frame member and a second rectangular substrate made of a resin and provided in a center portion of the first rectangular substrate; and that the first image quality evaluation patterns are fixed to an upper surface of the first rectangular substrate and the second image quality evaluation patterns are fixed to an upper surface of the second rectangular substrate.

The first rectangular substrate is preferably provided in a bottom portion of the box-shaped frame member.

It is preferred that the phantom for quality control of the present invention further comprises a rectangular top plate made of a resin and fixed to the opening portion of the box-shaped frame member so that the opening portion is closed, and that the rectangular top plate serves as a protection plate.

The first rectangular substrate and the rectangular top plate are preferably disposed on an inside with a preset distance in a thickness direction of the box-shaped frame member.

DETAILED DESCRIPTION OF THE PREFERRED EMBODIMENTS

The QC phantom of the present invention will now be described in detail with reference to embodiments showing in the accompanying drawings.

Figure 1:
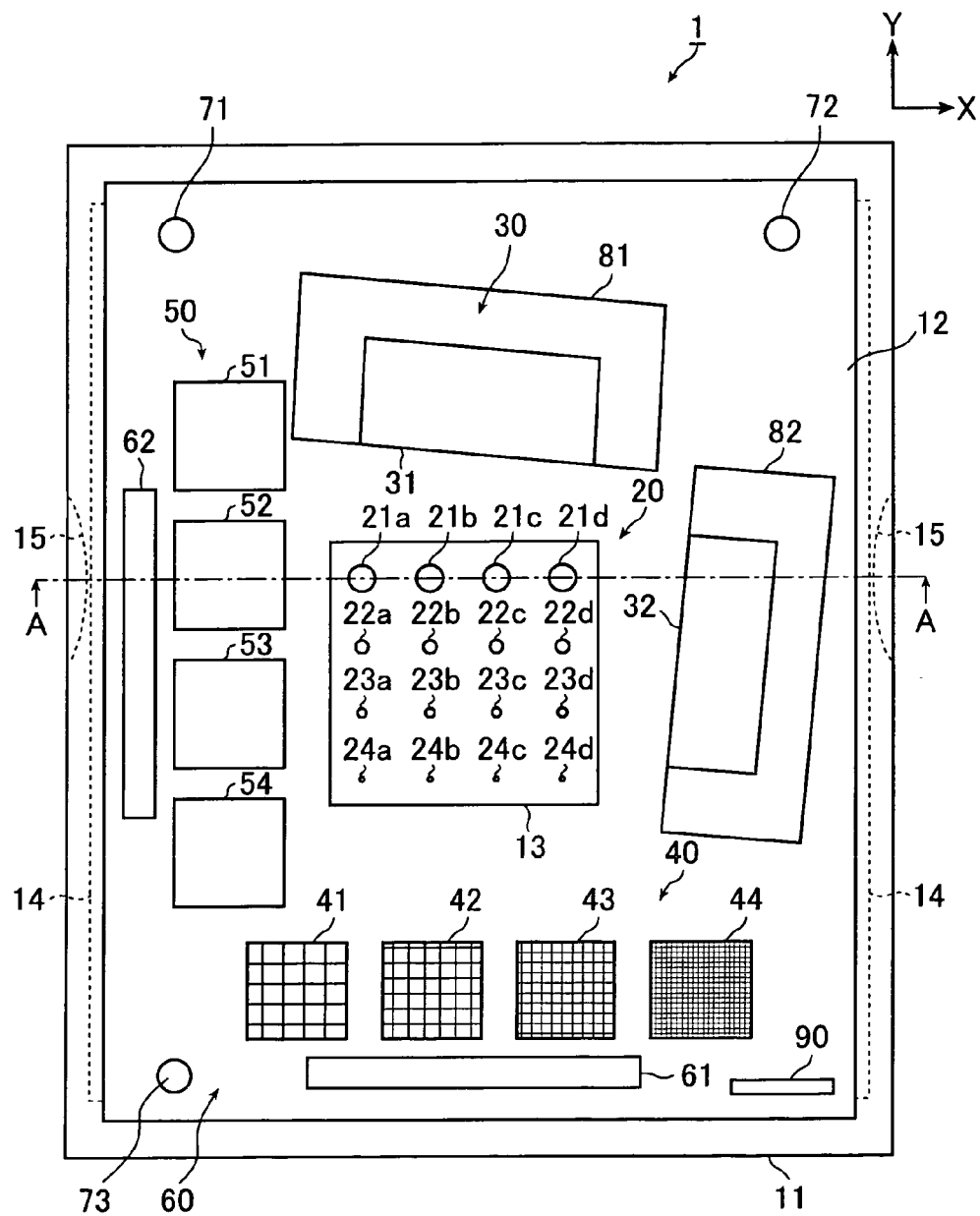
FIG. 1 is a plan view of a QC phantom according to a first embodiment of the present invention.
Figure 2:
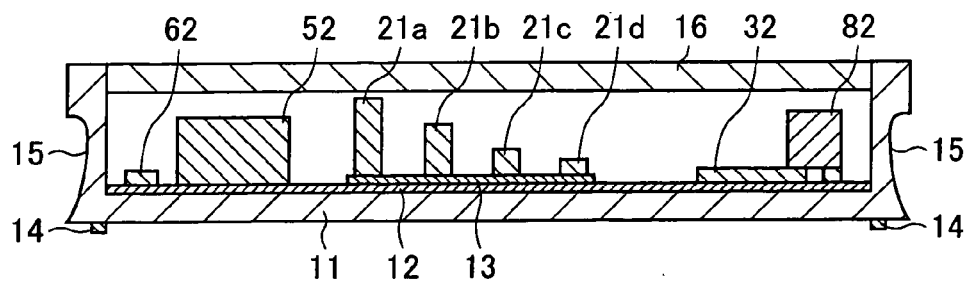
FIG. 2 is a cross-sectional view taken along the line A—A in FIG. 1.

FIG. 1 is a plan view of a QC phantom according to a first embodiment of the present invention and FIG. 2 is a cross-sectional view taken along the line A—A in FIG. 1.

A QC phantom 1 shown in FIGS. 1 and 2 is used to perform verification of the performance and invariance of a CR system. In the QC phantom 1, a rectangular-shaped copper plate 12 is provided as a substrate in the bottom portion of a box-shaped frame member 11. This copper plate 12 gives mechanical stability to the QC phantom 1 and imparts X-ray beam quality appropriate for image analysis.

A top plate 16 serving as a protection plate is fixed to an opening portion of the frame member 11 so that this opening portion is closed. Also, disposed in the frame member 11 are a Burger pattern 20 for visually evaluating the low contrast resolution of an image, an edge pattern 30 for quantitatively evaluating the sharpness of the image, a wire mesh pattern 40 for visually evaluating the sharpness of the image, a step-shaped pattern 50 for visually evaluating and quantitatively evaluating the linearity and dynamic range of the image, and a scale pattern 60 for quantitatively evaluating the scale factor of the image.

Further, narrow and long protrusions 14 for positioning the QC phantom 1 with respect to a cassette or a stimulable phosphor sheet are respectively provided for both the end sides on the underside of the frame member 11, and concave-shaped handgrip portions 15 for facilitating carrying of the QC phantom 1 are respectively formed at the center in the lower portions of both the sides of the frame member 11. Note that the positioning of the QC phantom 1 with respect to a cassette or a stimulable phosphor sheet is performed through fitting of the protrusions 14 into concave-shaped receiving portions provided in the cassette or the stimulable phosphor sheet. In the case of a cassette that is larger than the QC phantom 1, however, the positioning is performed through matching of the external shape of the QC phantom 1.

A substantially square resin plate 13 is provided as a substrate in the center portion of the copper plate 12. The Burger pattern 20 includes 16 step portions 21*a* to 21*d*, 22*a* to 22*d*, 23*a* to 23*d*, and 24*a* to 24*d* that are each made of an acrylic resin or the like and are welded and fixed on the resin plate 13 made of an acrylic resin, for instance. These step portions 21*a* to 21*d*, 22*a* to 22*d*, 23*a* to 23*d*, and 24*a* to 24*d* are arranged in a matrix manner so as to differ in their thicknesses in an X direction and differ in their sizes in a Y direction. With the Burger pattern 20 having such a construction, the low contrast resolution of an image is visually evaluated and the relative contrast and S/N ratio of a radiation imaging system are verified.

It should be noted here that at the time of welding of the Burger pattern 20 onto the resin plate 13, a welding agent, such as methylene chloride, is applied to predetermined locations of the Burger pattern 20 and/or the resin plate 13 and are rapidly solidified. The use of such a welding agent makes it possible to prevent capturing of the welding agent into an X-ray image and to realize strong bonding and fixation without using structural members such as screws.

Due consideration is given to the attachment or fixation of the resin plate 13 to or on the copper plate 12 to prevent a difference in coefficient of thermal expansion between the two plates from affecting the attachment or fixation. Although the state of attachment or fixation is not shown, for instance, the edge portion of one side of the resin plate 13 may only be bonded to the copper plate 12 to reduce any influence of the difference in coefficient of thermal expansion, or a region of the resin plate 13 which is apart from the image quality evaluation patterns and hence does not affect the image quality evaluation may be screwed onto the copper plate 12. Alternatively, the attachment or fixation can also be made by bonding the bonding surface of the resin plate 13 to the copper plate 12 using an elastic bonding agent. In this case, an elastic bonding agent can be used in the entire bonding surface of the resin plate 13 for bonding to the copper plate 12, but the elastic bonding agent is expensive and its use in the entire surface is not preferable from a cost standpoint. It is therefore preferable to use a bonding agent in a part of the bonding surface if the resin plate 13 can be attached to or fixed on the copper plate 12.

Also, the edge pattern 30, the wire mesh pattern 40, the step-shaped pattern 50, and the scale pattern 60 are each fixed at a predetermined position on the copper plate 12 using a bonding agent. Note that when such metal-based image quality evaluation patterns are fixed to the copper plate 12 serving as a substrate, a bonding agent is used. This is because the metal-based image quality evaluation patterns are relatively high in X-ray absorption factor, so that a high contrast X-ray image is obtained, making those patterns less susceptible to the influence of capturing of the bonding agent into the image. With this construction, it becomes possible to obtain a strong bonding strength without using structural members such as screws.

The edge pattern 30 is used as a reference for geometric measurement and has sharp angular edge portions 31 and 32 for MTF measurement in different directions. These angular edge portions 31 and 32 are each made of a tungsten plate and are provided with lead plates 81 and 82 on the outside thereof, respectively, so that the major portion of X-ray propagation therethrough is inhibited. With this construction, it becomes possible to suppress the influence of the peripheral environment and to evaluate sharpness with higher accuracy. Here, the MTF described above is obtained by differentiating the X-ray image of the edge pattern 30, obtaining a line spread function, and performing Fourier transform.

It is preferable that the wire mesh pattern 40 is a mesh made of steel. This wire mesh pattern 40 includes four mesh portions 41 to 44 having different sizes and enables a visual evaluation of the resolution (sharpness) of the CR system. It is possible to evaluate the resolution of the CR system through comparison of visibilities among the multiple mesh portions 41 to 44.

In this embodiment, the wire mesh pattern 40 includes the four mesh portions 41 to 44, thereby improving the accuracy of a resolution evaluation. However, it is also possible to perform more precise evaluation using five or more mesh portions having different sizes. Note that the sizes, thicknesses, and arrangement intervals of such meshes are not specifically limited and may be set at appropriate values.

In the step-shaped pattern 50, four rectangular-shaped copper plates 51 to 54 having different thicknesses are arranged in a step manner in the Y direction and are used to perform a visual evaluation and a quantitative evaluation of the linearity and dynamic range of an X-ray image. The intensity of X-rays passing through the copper plates 51 to 54 are in inverse proportion to their thicknesses, so that it is possible to realize intensity levels ranging from the maximum intensity to the minimum intensity using the respective copper plates 51 to 54. While the step-shaped pattern 50 includes the four copper plates 51 to 54 in this embodiment, the pattern 50 is not limited to this and may be constructed using copper plates having various sizes and thicknesses.

The scale pattern 60 includes a main scale 61 made of copper and provided so as to extend in the X direction and an auxiliary scale 62 made of copper and provided so as to extend in the Y direction, and is used to evaluate the scale factor of an image. Note that in FIG. 1, reference numerals 71, 72, and 73 each denote a marker used to perform alignment of the QC phantom 1 and to detect the positions of the various patterns. These markers are respectively provided in the corner portions of the copper plate 12 and facilitate automated processing at the time of computer processing of an image by enabling automatic detection of an error in installation direction to the cassette and confirmation of the positions of the various patterns. Also, reference numeral 90 represents a serial label on which a serial number has been printed.

Here, in the QC phantom of the present invention, a coefficient of linear expansion $\alpha_p$ of each of corresponding image quality evaluation patterns which are fixed to each substrate and a coefficient of linear expansion $\alpha_s$ of each substrate to which the corresponding image quality evaluation patterns are fixed, must be satisfied in a relation of $|\alpha_p - \alpha_s| \leq 5 \times 10^{-5}$.

The coefficient of linear expansion $\alpha(K^{-1})$ is represented by the following equation:

$$\alpha = (1/l) = (dl/dT) \tag{1}$$

where l is the length of a material (forming material of image quality evaluation pattern, substrate) and T is the absolute temperature (K).

Table 1 below shows α values of materials very often used in the QC phantom.

TABLE 1

| Material | Coefficient of linear expansion $\alpha(K^{-1})$ |
|---|---|
| Copper | $1.65 \times 10^{-5}$ |
| Aluminum | $2.31 \times 10^{-5}$ |
| Tungsten | $0.45 \times 10^{-5}$ |
| Stainless steel | $1.47 \times 10^{-5}$ |
| Lead | $2.89 \times 10^{-5}$ |
| Acrylic resin | $7 \times 10^{-5}$ |
| Polymethyl methacrylate | $8 \times 10^{-5}$ |

It is preferable that the coefficient of linear expansion $\alpha_p$ of each of the corresponding image quality evaluation patterns and the coefficient of linear expansion $\alpha_s$ of each substrates are satisfied in a relation of $|\alpha_p-\alpha_s|\leq 2.5\times 10^{-5}$, more preferably, $|\alpha_p-\alpha_s|\leq 1.5\times 10^{-5}$.

The QC phantom 1 has a construction where the edge pattern 30, the wire mesh pattern 40, the step-shaped pattern 50, and the scale pattern 60 that are each an image quality evaluation pattern made of a metal are fixed on the copper plate 12 serving as a substrate and the Burger pattern 20 made of a resin is welded onto the resin plate 13 that is another substrate. With this construction in which the image quality evaluation pattern and the substrate are satisfied in the above relation of $|\alpha_p-\alpha_s|\leq 5\times 10^{-5}$, it becomes possible to prevent cracking and peeling of the image quality evaluation patterns due to differences in coefficient of thermal expansion and to suppress capturing of construction members other than the image quality evaluation patterns into an X-ray image.

Next, a QC phantom according to a second embodiment of the present invention will be described by giving the same reference numerals to the same construction members as those of FIGS. 1 and 2. Note that FIG. 3 is a plan view of the QC phantom according to the second embodiment of the present invention and FIG. 4 is a cross-sectional view taken along the line B—B in FIG. 3.

Figure 3:
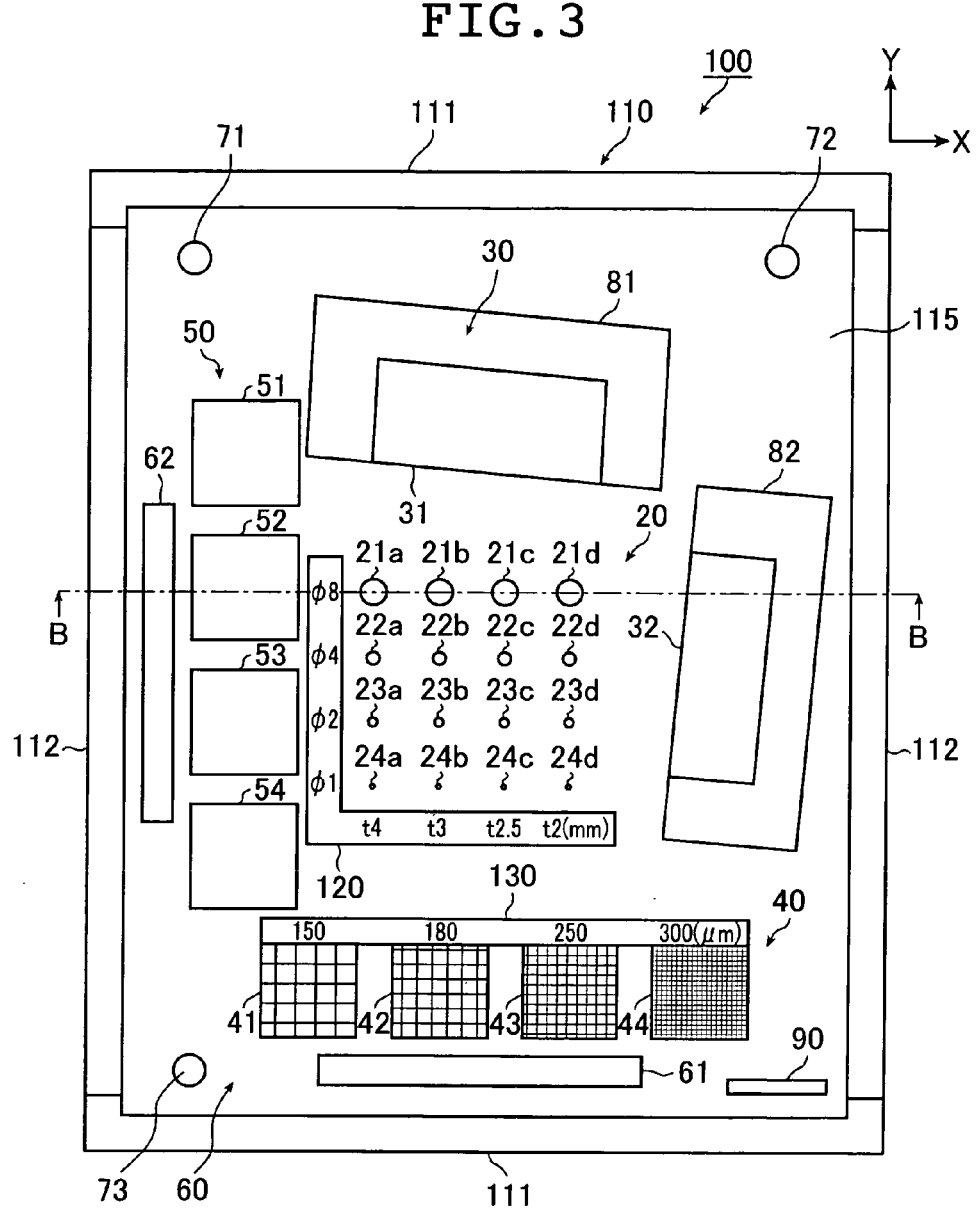
FIG. 3 is a plan view of a QC phantom according to a second embodiment of the present invention.
Figure 4:
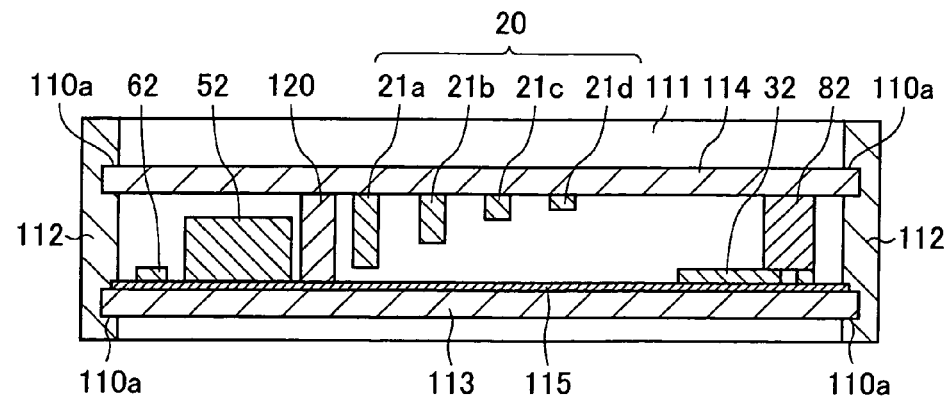
FIG. 4 is a cross-sectional view taken along the line B—B in FIG. 3.

A QC phantom 100 shown in FIGS. 3 and 4 has a frame member 110 formed by combining upper and lower frames 111 with side frames 112 into a rectangular shape. In this frame member 110, a supporting plate 113 made of an acrylic resin and a top plate 114 also made of an acrylic resin are placed parallel to each other while being spaced apart from each other in the vertical direction (thickness direction of the frame member 110). Also, one pair of upper and lower annular grooves 110a are formed in the inner peripheral surface of the frame member 110 at positions slightly inside from the upper and lower ends thereof.

On the supporting plate 113, a copper plate 115 is provided as a substrate and the peripheral ends of the supporting plate 113, the copper plate 115, and the top plate 114 are fitted into the annular grooves 110a. Here, the peripheral ends of the supporting plate 113, the copper plate 115, and the top plate 114 are only partially fixed to the annular grooves 110a so that it is possible to absorb distortion due to differences in the coefficient of thermal expansion among the frame member 110, the supporting plate 113, the copper plate 115, and the top plate 114.

Disposed at predetermined positions on the copper plate 115 are an edge pattern 30 made of tungsten and having angular edge portions 31 and 32 for MTF measurement in different directions which are surrounded by lead plates 81 and 82 on the outside thereof, respectively, so that the major portion of X-ray propagation therethrough is inhibited, a wire mesh pattern 40 including four mesh portions 41 to 44 made of steel and having different sizes, a step-shaped pattern 50 in which four rectangular-shaped copper plates 51 to 54 having different thicknesses are arranged in a step manner in a Y direction, a scale pattern 60 including a main scale 61 made of copper and provided so as to extend in an X direction and an auxiliary scale 62 made of copper and provided so as to extend in the Y direction, and markers 71, 72, and 73 respectively provided in the corner portions of the copper plate 115. Note that when such metal-based image quality evaluation patterns are fixed to the copper plate 115 that is a substrate, a bonding agent is used. With this construction, strong fixation is achieved without using structural members such as screws. Also, the reason why it is possible to perform the fixation using the bonding agent is that as described above, with the metal-based image quality evaluation patterns having a relatively high X-ray absorption factor, a high contrast X-ray image is obtained, making those patterns less susceptible to the influence of capturing of the bonding agent into the image.

A Burger pattern 20 made of an acrylic resin is welded in the center portion of the top plate 114. This Burger phantom 20 includes 16 step portions 21a to 21d, 22a to 22d, 23a to 23d, and 24a to 24d, with these step portions 21a to 21d, 22a to 22d, 23a to 23d, and 24a to 24d being arranged in a matrix manner so as to differ in their thicknesses in the X direction and differ in their sizes in the Y direction. When the Burger pattern 20 is welded as described above, it becomes possible to suppress capturing of construction members other than the Burger pattern 20 into an X-ray image and to obtain a strong bonding strength.

A display member 120 for displaying the sizes and thicknesses of the step portions 21a to 24d of the Burger pattern 20 and a display member 130 for displaying the mesh sizes of the mesh portions 41 to 44 are provided between the top plate 114 and the copper plate 115, with these display members 120 and 130 also serving as reinforcers of the QC phantom 100. Incidentally, if the thicknesses of the lead plates 81 and 82 are set so that these lead plates 81 and 82 reach the top plate 114, these plates also serve as reinforcers of the QC phantom 100. With this construction, it also becomes possible to prevent redundant capturing of dedicated reinforcers into an X-ray image. Also, a serial label 90 is stuck in the lower right corner portion of the top plate 114.

As described above, the QC phantom 100 has a construction in which the multiple image quality evaluation patterns are disposed in a hollow portion defined by the frame member 110, the supporting plate 113, and the top plate 114. In particular, the Burger pattern 20 is fixed to the top plate 114. With this construction, it becomes possible to reduce a dead space to a minimum level and to obtain a thin and lightweight phantom. Also, the supporting plate 113 and the top plate 114 are positioned inside the top and bottom ends of the frame member 110. With this construction, the phantom main body is prevented from directly contacting a cassette or a stimulable phosphor sheet. As a result, it becomes possible to suppress damage to the QC phantom 100, the cassette, and the stimulable phosphor sheet.

Also, as in the case of the QC phantom 1, the edge pattern 30, the wire mesh pattern 40, the step-shaped pattern 50, and the scale pattern 60 that are each made of a metal are fixed on the copper plate 115 serving as a substrate, and the Burger pattern 20 made of a resin is fixed to the top plate 114 made of a resin that is another substrate. That is, each image quality evaluation pattern is fixed to a substrate made of the same material as the material forming the image quality evaluation pattern. With this construction, it becomes possible to prevent cracking and peeling of the image quality evaluation patterns due to differences in coefficient of thermal expansion and to firmly fix the image quality evaluation patterns to the substrates. Also, construction members other than the image quality evaluation patterns are not captured in an X-ray image and therefore the evaluation is not hindered.

In the above-mentioned QC phantoms 1 and 100 in the first and second embodiments, image quality evaluation patterns made of metals such as the edge pattern 30, wire mesh pattern 40, step-shaped pattern 50 and scale pattern 60 are used for the image quality evaluation patterns to be fixed on the copper plate 12 or 115 serving as the substrate. The Burger pattern 20 made of a resin is used for the image quality evaluation pattern fixed on the resin plate 13 or the top plate 114 made of a resin that is another substrate. However, this is not the sole case of the present invention. The image quality evaluation patterns may be produced using materials having high radiation absorption rates instead of the image quality evaluation patterns made of metals, or the Burger pattern 20 may de produced by using a material having a low radiation absorption rate instead of the Burger pattern 20 made of a resin. To be more specific, the material of the Burger pattern 20 is not limited to resins but a material having a relatively low radiation absorption rate such as ceramic may be used for its production.

Figure 5:
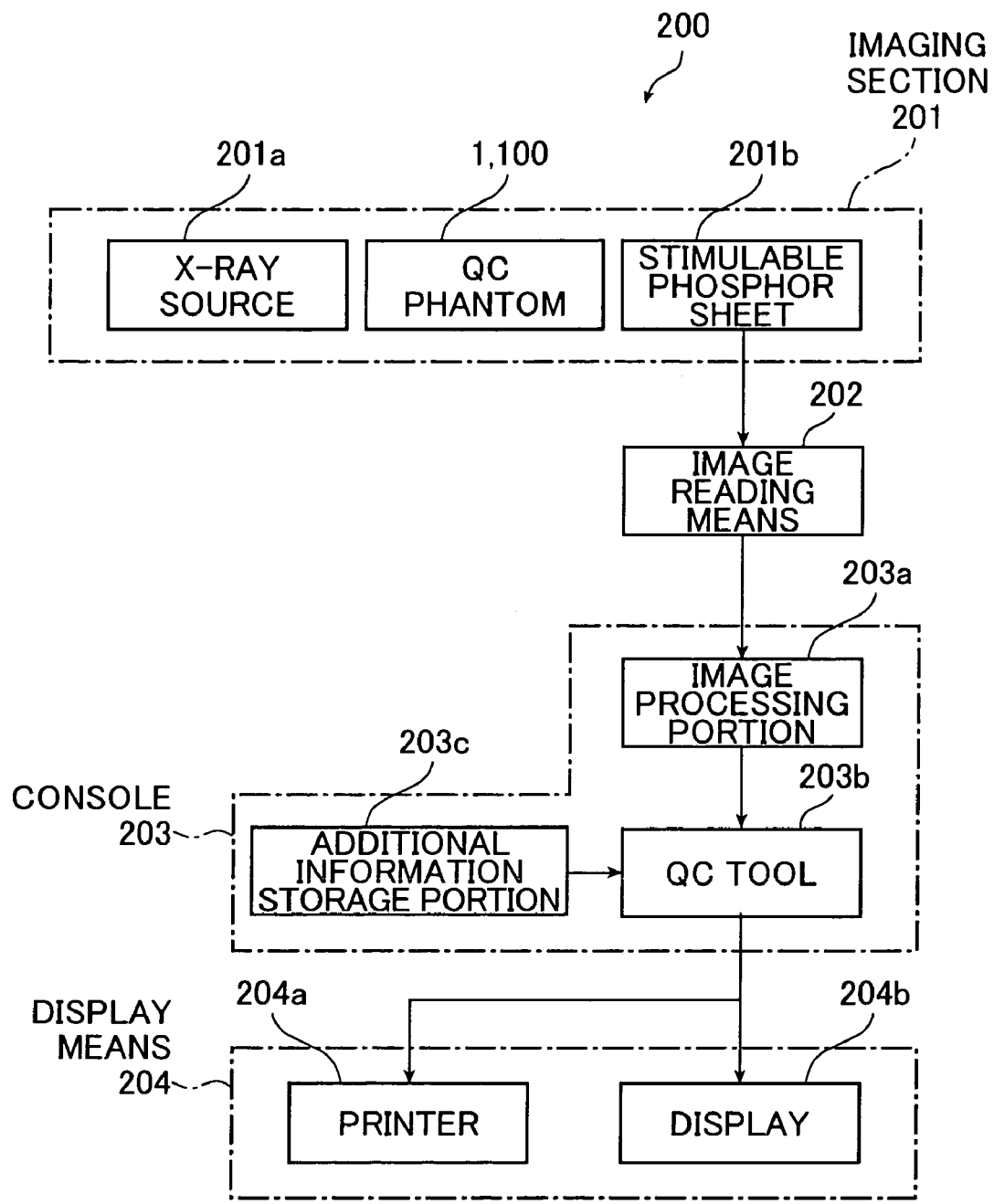
FIG. 5 is a block diagram of a CR system having the QC phantom shown in FIG. 1 or 3.

FIG. 5 is a block diagram of a CR system that photographs the QC phantom 1, 100 described above.

The CR system 200 shown in FIG. 5 includes an imaging section 201 for photographing the QC phantom 1, 100 as a subject and obtaining an image thereof, an image reading means 202 for reading image data of the obtained image, a console 203 for performing processing on the read image data, performing evaluation computation for quantitative evaluation of the image, and outputting additional information concerning the image, and display means 204 for displaying the image of the QC phantom 1, 100 together with the additional information.

The imaging section 201 has an X-ray source 201a, which projects X rays onto the QC phantom 1, 100, and a recording medium, such as a stimulable phosphor sheet 201b, on which X rays having passed through the QC phantom 1, 100 are to be recorded.

The image reading means 202 irradiates excitation light onto the stimulable phosphor sheet 201b, on which an X-ray image has been recorded, and reads photostimulated luminescence light generated from the stimulable phosphor sheet 201b, thereby reading data of the image photographed on the stimulable phosphor sheet 201b. For instance, the image reading means 202 is a reading head that uses a line light source produced by arranging excitation light sources, such as LEDs, in a main scanning direction as a light source of the excitation light and has a line sensor, such as a line CCD, provided so as to extend in the main scanning direction. With this construction, while the reading head and the stimulable phosphor sheet 201b are relatively moved in an auxiliary scanning direction orthogonal to the main scanning direction, the excitation light emitted from the line light source is made incident on the stimulable phosphor sheet 201b and photostimulated luminescence light generated from the stimulable phosphor sheet 201b is read using the line sensor.

Alternatively, the image reading means 202 uses a laser beam as the excitation light and deflects the laser beam in the main scanning direction so that the laser beam is incident on the stimulable phosphor sheet 201b. When doing so, the stimulable phosphor sheet 201b is conveyed in the auxiliary scanning direction, thereby two-dimensionally scanning the stimulable phosphor sheet 201b with the excitation light. Then, the photostimulated luminescence light generated in this manner is propagated by a light-propagating device and is detected using a photodetector, such as a photomultiplier, and an AD converter, thereby reading the data of the image photographed on the stimulable phosphor sheet 201b.

The console 203 is constructed using a personal computer (PC), for instance, and is connected to the image reading means 202 and the display means 204 through known communication means such as a computer communication network. Also, the console 203 includes an image processing portion 203a for performing image processing of the image data read by the image reading means 202, a QC tool 203b that performs a quantitative evaluation (QC computation) of the image, and an additional information storage portion 203c for recording additional information concerning the image.

The QC tool 203b is provided with software for quantitatively evaluating images of the various image quality evaluation patterns of the QC phantom 1, 100. The QC tool 203 receives an image of the QC phantom 1, 100 processed by the image processing portion 203a, performs a quantitative evaluation of images of the various image quality evaluation patterns, and displays a result of the evaluation using the display means 204. Also, when a visual evaluation is performed, the images are displayed using the display means 204. Note that the quantitative evaluation software has various signal processing algorithms, with these algorithms having every logic means for calculating required quality measurement of the radiation imaging system 200 when applied to the images of the various image quality evaluation patterns of the QC phantom 1, 100. Also, the QC tool 203b is incorporated into the console 203 in this embodiment, but this is not the sole case of the present invention. This tool 203b may be incorporated into a host computer managing the whole of the system, for instance. Also, a PC, on which only the QC tool 203b is installed, may be used.

The additional information storage portion 203c stores: imaging conditions used at the time of X-ray photographing such as an X-ray tube voltage and a distance between an X-ray source and a subject; image reading conditions used in the image reading means 202; image processing conditions used in the image processing portion 203a; and image display conditions used in the display means 204 such as the number of pixels, the number of steps of gradation, and the presence or absence of image processing. This additional information is read out to the QC tool 203b as necessary.

The display means 204 includes a printer 204a, such as a laser printer, and a display 204b such as a CRT display or a liquid crystal display. With this construction, the display means 204 outputs the image of the QC phantom 1, 100 and the additional information as a visible image.

At the time of imaging of the QC phantom 1, 100 with the CR system 200 constructed in the manner described above, first, the QC phantom 1, 100 is placed between the X-ray source 201a and the stimulable phosphor sheet 201b, and X rays are projected from the X-ray source 201a. When the X-rays pass through the QC phantom 1, 100, their intensities are attenuated and inhibited by the various image quality evaluation patterns constituting the QC phantom 1, 100. Following this, the intensities are converted into various spatial values and are recorded on the stimulable phosphor sheet 201b.

Then, the X-ray intensities recorded on the stimulable phosphor sheet 201b are read by the image reading means 202. For instance, the image reading means 202 irradiates the stimulable phosphor sheet 201b with a laser beam, thereby converting the recorded X-ray intensity into photostimulated luminescence light. Then, the photostimulated luminescence light is read as digital image data using a photodetector and the digital data is recorded on an information recording medium.

The image processing portion 203a performs image processing, such as gradation processing, on read image data of the image quality evaluation patterns. Then, the QC tool 203b quantitatively evaluates the processed image based on various image quality evaluation items. When doing so, if necessary, some of the additional information is read out from the additional information storage portion 203c and is applied to the QC computation. Also, the image is visually evaluated through printing on a film by the printer 204*a* or displaying on the display 204*b*. That is, through the quantitative evaluation and visual evaluation of the images of the various image quality evaluation patterns of the QC phantom 1, 100, the performance and invariance of the CR system 200 are verified.

The QC phantom according to the present invention has been described in detail with reference to the embodiments, although the present invention is not limited to the QC phantoms described in the embodiments. It is possible to make various design changes without departing from the gist of the present invention described in the appended claims.

For instance, in the embodiments described above, each image quality evaluation pattern is fixed to a substrate through welding or bonding. However, the image quality evaluation pattern may be integrally molded with the substrate or formed through cutting by an NC machine tool or the like.

Also, the QC phantom 1, 100 of the present invention is usable not only in the CR system described above but also in a CR system that uses a flat panel detector (FPD).

Needless to say, in the embodiments described above, the coefficients of linear expansion $\alpha_p$ of the various image quality evaluation patterns and the coefficient of linear expansion $\alpha_s$ of the substrate, to which the image quality evaluation patterns are fixed, satisfy a relation of "$|\alpha_p - \alpha_s| \leq 5 \times 10^{-5}$".

As can be understood from the above description, with the construction of the QC phantom of the present invention, it becomes possible to prevent cracking and peeling of the image quality evaluation patterns due to differences in coefficient of thermal expansion. Also, no construction members other than the image quality evaluation patterns are captured into an X-ray image, so that it becomes possible to perform a more accurate invariance test.

What is claimed is:

1. A phantom for quality control used to perform verification of performance and invariance of a radiation imaging system, comprising:
    substrates; and
    image quality evaluation patterns fixed to said substrates, said image quality evaluation patterns being photographed with said radiation imaging system and pattern images obtained by photographing said image quality evaluation patterns being evaluated based on image quality evaluation items,
    wherein a coefficient of linear expansion $\alpha_p$ of each of corresponding image quality evaluation patterns which are fixed to each of said substrates and a coefficient of linear expansion $\alpha_s$ of each of said substrates to which said corresponding image quality evaluation patterns are fixed, are in a relation of $|\alpha_p - \alpha_s| \leq 5.0 \times 10^{-5}$, and said corresponding image quality evaluation patterns are directly fixed to one corresponding substrate of said substrates.

2. The phantom for quality control according to claim 1, wherein said coefficient of linear expansion $\alpha_p$ of each of said corresponding image quality evaluation patterns and said coefficient of linear expansion $\alpha_s$ of each of said substrates are in a relation of $|\alpha_p - \alpha_s| \leq 2.5 \times 10^{-5}$.

3. The phantom for quality control according to claim 1, wherein said coefficient of linear expansion a of each of corresponding image quality evaluation patterns and said coefficient of linear expansion $\alpha_s$ of each of said substrates are in a relation of $|\alpha_p - \alpha_s| \leq 1.5 \times 10^{-5}$.

4. The phantom for quality control according to claim 1, wherein said image quality evaluation patterns are fixed to said substrates by welding or bonding an image quality evaluation pattern on a substrate, alternatively, by molding integrally said image quality evaluation pattern with said substrate or forming said image quality evaluation pattern and said substrate through cutting by an NC machine tool.

5. The phantom for quality control according to claim 1, wherein said image quality evaluation patterns comprises:
    first image quality evaluation patterns each made of a material or materials having a high radiation absorption rate; and
    second image quality evaluation patterns each made of a material or materials having a low radiation absorption rate.

6. A phantom for quality control used to perform verification of performance and invariance of a radiation imaging system, comprising:
    substrates, and
    image quality evaluation patterns fixed to said substrates, said image quality evaluation patterns being photographed with said radiation imaging system and pattern images obtained by photographing said image quality evaluation patterns being evaluated based on image quality evaluation items,
    wherein a coefficient of linear expansion $\alpha_p$ of each of corresponding image quality evaluation patterns which are fixed to each of said substrates and a coefficient of linear expansion $\alpha_s$ of each of said substrates to which said corresponding image quality evaluation patterns are fixed, are in a relation of:

$|\alpha_p - \alpha_s| \leq 1.5 \times 10^{-5}$, wherein said image quality evaluation patterns comprises:
    first image quality evaluation patterns each made of a material or materials having a high radiation absorption rate; and
    second image quality evaluation patterns each made of a material or materials having a low radiation absorption rate, and
    wherein said first image quality evaluation patterns are made of a metal or metals and said second image quality evaluation patterns are made of a resin or resins.

7. The phantom for quality control according to claim 6, further comprising:
    a rectangular frame member having a hollow portion,
    wherein said substrates includes:
    a first rectangular substrate made of a metal and provided in said hollow portion of said rectangular frame member; and
    a rectangular top plate made of a resin and placed in said hollow portion of said rectangular frame member to oppose said first rectangular substrate with a preset distance between said rectangular top plate and said first rectangular substrate, said rectangular top plate serving as a second substrate,
    wherein, in a hollow space formed by said rectangular frame member, said first rectangular substrate and said rectangular top plate, said first image quality evaluation patterns are fixed to an upper surface of said first rectangular substrate and said second image quality evaluation patterns are fixed to a lower surface of said rectangular top plate.

8. The phantom for quality control according to claim 7, wherein peripheral ends of said first rectangular substrate and said rectangular top plate are partially fixed to said rectangular frame member under a state where said peripheral ends are fitted into an inner peripheral portion of said rectangular frame member.

9. The phantom for quality control according to claim 8, wherein said first rectangular substrate and said rectangular top plate are disposed on an inside in a thickness direction of said rectangular frame member.

10. The phantom for quality control according to claim 7 further comprising:
a supporting plate for supporting said first rectangular substrate,
wherein said supporting plate is made of a resin and placed in said hollow portion of said rectangular frame member to oppose said first rectangular substrate, and
wherein said first rectangular substrate is mounted on said supporting plate.

11. The phantom for quality control according to claim 6, further comprising:
a box-shaped frame member having an opening portion, wherein said substrates includes:
a first rectangular substrate made of a metal and provided in said opening portion of said box-shaped frame member; and
a second rectangular substrate made of a resin and provided in a center portion of said first rectangular substrate, and
wherein said first image quality evaluation patterns are fixed to an upper surface of said first rectangular substrate and said second image quality evaluation patterns are fixed to an upper surface of said second rectangular substrate.

12. The phantom for quality control according to claim 11, wherein said first rectangular substrate is provided in a bottom portion of said box-shaped frame member.

13. The phantom for quality control according to claim 11, further comprising:
a rectangular top plate made of a resin and fixed to said opening portion of said box-shaped frame member so that said opening portion is closed, said rectangular top plate serving as a protection plate.

14. The phantom for quality control according to claim 13, wherein said first rectangular substrate and said rectangular top plate are disposed on an inside with a preset distance in a thickness direction of said box-shaped frame member.

15. A phantom for quality control used to perform verification of performance and invariance of a radiation imaging system, comprising:
substrates; and
image quality evaluation patterns fixed to said substrates, said image quality evaluation patterns being photographed with said radiation imaging system and pattern images obtained by photographing said image quality evaluation patterns being evaluated based on image quality evaluation items, wherein the image quality evaluation patterns are made of at least one of metal and resin.

16. The phantom of claim 15 wherein the image quality evaluation patterns comprise a first image quality evaluation pattern comprising metal and a second image quality evaluation pattern comprising resin.

17. A phantom for quality control used to perform verification of performance and invariance of a radiation imaging system, comprising:
substrates; and
image quality evaluation patterns fixed to said substrates, said image quality evaluation patterns being photographed with said radiation imaging system and pattern images obtained by photographing said image quality evaluation patterns being evaluated based on image quality evaluation items,
wherein a coefficient of linear expansion $\alpha_p$ of each of corresponding image quality evaluation patterns which are fixed to each of said substrates and a coefficient of linear expansion $\alpha_s$ of each of said substrates to which said corresponding image quality evaluation patterns are fixed, are in a relation of $$|\alpha_p - \alpha_s| \leq 1.5 \times 10^{-5}.$$

18. The phantom for quality control according to claim 17, wherein said image quality evaluation patterns are fixed to said substrates by welding or bonding an image quality evaluation pattern on a substrate, alternatively, by molding integrally said image quality evaluation pattern with said substrate or forming said image quality evaluation pattern and said substrate through cutting by an NC machine tool.

19. The phantom for quality control according to claim 17, wherein said image quality evaluation patterns comprises:
first image quality evaluation patterns each made of a material or materials having a high radiation absorption rate; and
second image quality evaluation patterns each made of a material or materials having a low radiation absorption rate.

* * * * *